(12) United States Patent
Lambalot et al.

(10) Patent No.: US 10,105,622 B2
(45) Date of Patent: Oct. 23, 2018

(54) FILTRATION CASSETTE AND A STACK OF FILTRATION CASSETTES

(71) Applicant: GE HEALTHCARE BIO-SCIENCES AB, Uppsala (SE)

(72) Inventors: Charles Lambalot, Mansfield, MA (US); William Larsen, Westborough, MA (US)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 700 days.

(21) Appl. No.: 14/403,673

(22) PCT Filed: May 29, 2013

(86) PCT No.: PCT/SE2013/050611
§ 371 (c)(1),
(2) Date: Nov. 25, 2014

(87) PCT Pub. No.: WO2013/180632
PCT Pub. Date: Dec. 5, 2013

(65) Prior Publication Data
US 2015/0165353 A1    Jun. 18, 2015

Related U.S. Application Data

(60) Provisional application No. 61/652,873, filed on May 30, 2012.

(30) Foreign Application Priority Data

Jun. 26, 2012    (SE) ........................................ 1250690

(51) Int. Cl.
*B01D 29/56*    (2006.01)
*C12M 1/00*    (2006.01)
(Continued)

(52) U.S. Cl.
CPC ............. *B01D 29/56* (2013.01); *B01D 29/88* (2013.01); *C12M 23/42* (2013.01); *C12M 47/10* (2013.01);
(Continued)

(58) Field of Classification Search
CPC ...... B01D 25/12; B01D 25/122; B01D 25/21; B01D 25/215; B01D 29/001; B01D 29/39;
(Continued)

(56) References Cited

U.S. PATENT DOCUMENTS 6,139,757 A    10/2000  Ohmura et al.
6,180,002 B1 *  1/2001  Higgins ............... B01D 25/215
                                                100/211
(Continued)

FOREIGN PATENT DOCUMENTS

EP    0806475    11/1997
EP    0987034     3/2000
(Continued)

OTHER PUBLICATIONS

Office Action issued in corresponding CN Application No. 201380028129.7, filed May 29, 2013 (dated Oct. 28, 2015).
PCT/SE2013/050611 ISRWO dated Sep. 27, 2013.

*Primary Examiner* — Pranav N Patel

(57) ABSTRACT

The invention discloses a normal flow filtration cassette (1) stackable with like cassettes, said cassette comprising: at least three port conduits (2,3,4); an inlet chamber (5) in fluid communication at least with a first of said port conduits (2); an outlet chamber (6) in fluid communication at least with a second of the port conduits (3); and a filter medium (7) between said inlet chamber and said outlet chamber, wherein said at least three port conduits (2,3,4) are each in fluid communication with a corresponding inlet port (8,9,10) and are each in fluid communication also with one of a corre- (Continued)

sponding set of outlet ports (11,12,13), and wherein each of said set of inlet ports (8,9 10) is arranged to cooperate with a respective complementary outlet port of an adjacent like cassette when in a stack and said outlet ports (11,12,13) are each arranged to cooperate with a respective complementary inlet port of a further adjacent like cassette when in a stack.

18 Claims, 8 Drawing Sheets

(51) Int. Cl.
*B01D 29/88* (2006.01)
*C12M 3/00* (2006.01)
*B01D 29/05* (2006.01)
*B01D 63/08* (2006.01)

(52) U.S. Cl.
CPC ............. *C12M 47/12* (2013.01); *B01D 63/08* (2013.01); *B01D 63/082* (2013.01); *B01D 63/084* (2013.01)

(58) Field of Classification Search
CPC .. B01D 29/0095; B01D 63/08; B01D 63/081; B01D 63/082; B01D 63/084; B01D 63/087; B01D 2315/08; B01D 2315/10; B01D 2313/08; B01D 2313/06
See application file for complete search history.

(56) References Cited

U.S. PATENT DOCUMENTS

| | | | |
|---|---|---|---|
| 6,209,727 | B1 | 4/2001 | Henttonen et al. |
| 6,679,529 | B2* | 1/2004 | Johnson ................ A61M 39/18 285/3 |
| 6,712,966 | B1 | 3/2004 | Pulek et al. |
| 6,939,466 | B2 | 9/2005 | Pulek et al. |
| 2006/0091074 | A1* | 5/2006 | Pedersen .............. B01D 61/142 210/636 |
| 2007/0056894 | A1* | 3/2007 | Connors, Jr. ........ B01D 63/081 210/321.75 |
| 2010/0181248 | A1* | 7/2010 | Rautio ................. B01D 63/081 210/490 |
| 2010/0028266 | A1 | 11/2010 | Hunt |
| 2010/0282663 | A1 | 11/2010 | Hunt |

FOREIGN PATENT DOCUMENTS

| | | |
|---|---|---|
| EP | 0897318 B1 | 1/2006 |
| EP | 1637213 | 3/2006 |
| EP | 1967244 | 9/2008 |
| EP | 1974801 | 10/2008 |
| JP | 10-137557 A | 5/1998 |
| JP | 2000-083649 A | 3/2000 |
| JP | 2001504750 A | 4/2001 |
| WO | 94/08173 A1 | 4/1994 |
| WO | 96/30076 A1 | 10/1996 |
| WO | 97/32649 | 9/1997 |
| WO | 02/076592 | 10/2002 |

\* cited by examiner

FILTRATION CASSETTE AND A STACK OF FILTRATION CASSETTES

This application is a filing under 35 U.S.C. 371 of international application number PCT/SE2013/050611, filed May 29, 2013, which claims priority to Swedish application number 1250690-3 filed Jun. 26, 2012 and to U.S. application No. 61/652,873 filed May 30, 2012, the entire disclosure of which is hereby incorporated by reference.

TECHNICAL FIELD OF THE INVENTION

The present invention relates to filtration, and more particularly to filtration cassettes for clarification of bioprocess feeds. The invention also relates to stacks of filtration cassettes, to methods of clarification of bioprocess feeds with such stacks and to methods of selecting stacks for clarification of bioprocess feeds.

BACKGROUND OF THE INVENTION

Biopharmaceuticals such as protein drugs, vaccines etc are usually manufactured by cell culture and purified downstream by chromatography and other methods. Before the downstream purification, all particulates from the cell culture such as cells, cell debris etc must be removed in one or more clarification steps. At least one of these clarification steps normally involves depth filtration and to obtain a good clarification result with minimum clogging of the filter material, serial filtration through depth filter materials with decreasing pore size ratings is commonly used.

Stackable depth filter cassettes or capsules provide convenience for the user compared to traditional lenticular filter stacks in reusable housings. Several such stackable cassettes/capsules have been disclosed, see e.g. US20100282663, EP1967244A1, etc. They often contain a series of depth filter materials with decreasing pore size in each cassette/capsule to decrease clogging of the finer filter materials and there are also limited possibilities of combining different filter materials within stacks.

As the properties of bioprocess feeds can vary dramatically depending on the cell type used, the cell culture conditions, any pretreatments before depth filter clarification etc, there is a high demand for flexibility in the design of depth filtration setups in order to provide efficient clarification without severe clogging and at the same time minimizing the filter surface used to keep costs down. Current cassettes and capsules have limitations in this respect in that they only provide fixed 1:1 area ratios between coarse and fine filters, which leads to overdimensioning of one filter type and possibly underdimensioning of the other type. This leads to inefficient filtration processes and accordingly there is a need to provide a cassette or capsule system with improved flexibility.

SUMMARY OF THE INVENTION

One aspect of the invention is to provide a stackable normal flow filtration cassette allowing flexible assembly of filter modules with combinations of filter media in different area ratios. This is achieved with a cassette as defined in claim 1.

One advantage is that cassettes with different filter media can be combined with either parallel or serial flow-paths or combinations thereof. This allows tailoring of filter modules for particular feeds. A further advantage is that high clamping forces are not needed to hold a stack of cassettes together—a simple frame construction is sufficient. Yet another advantage is that specially designed manifolds are not needed and that sanitary couplings used in disposable bioprocessing can be directly applied on the cassettes.

A second aspect of the invention is to provide a filter module which can be flexibly assembled with combinations of filter media. This is achieved with a stack of cassettes as defined in the claims.

A third aspect of the invention is to provide an efficient method for clarification of bioprocess feeds. This is achieved with a method as defined in the claims.

A fourth aspect of the invention is to provide a convenient method of designing filter modules for clarification of bioprocess feeds. This is achieved with a method as defined in the claims.

Further suitable embodiments of the invention are described in the dependent claims.

DEFINITIONS

Figure 1:
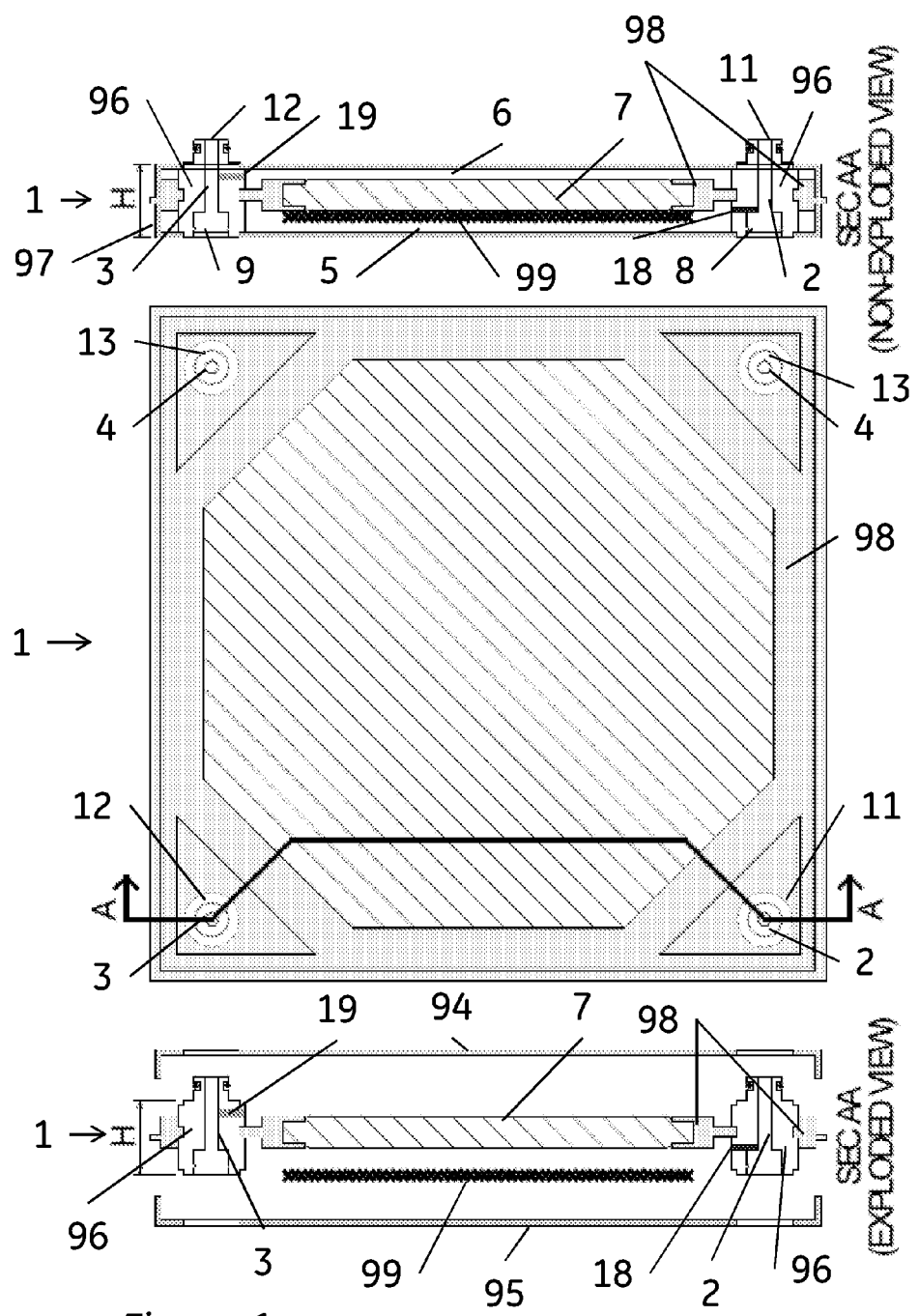
FIG. 1 shows a cassette according to the invention in exploded side view, top view and non-exploded side view.
Figure 2:
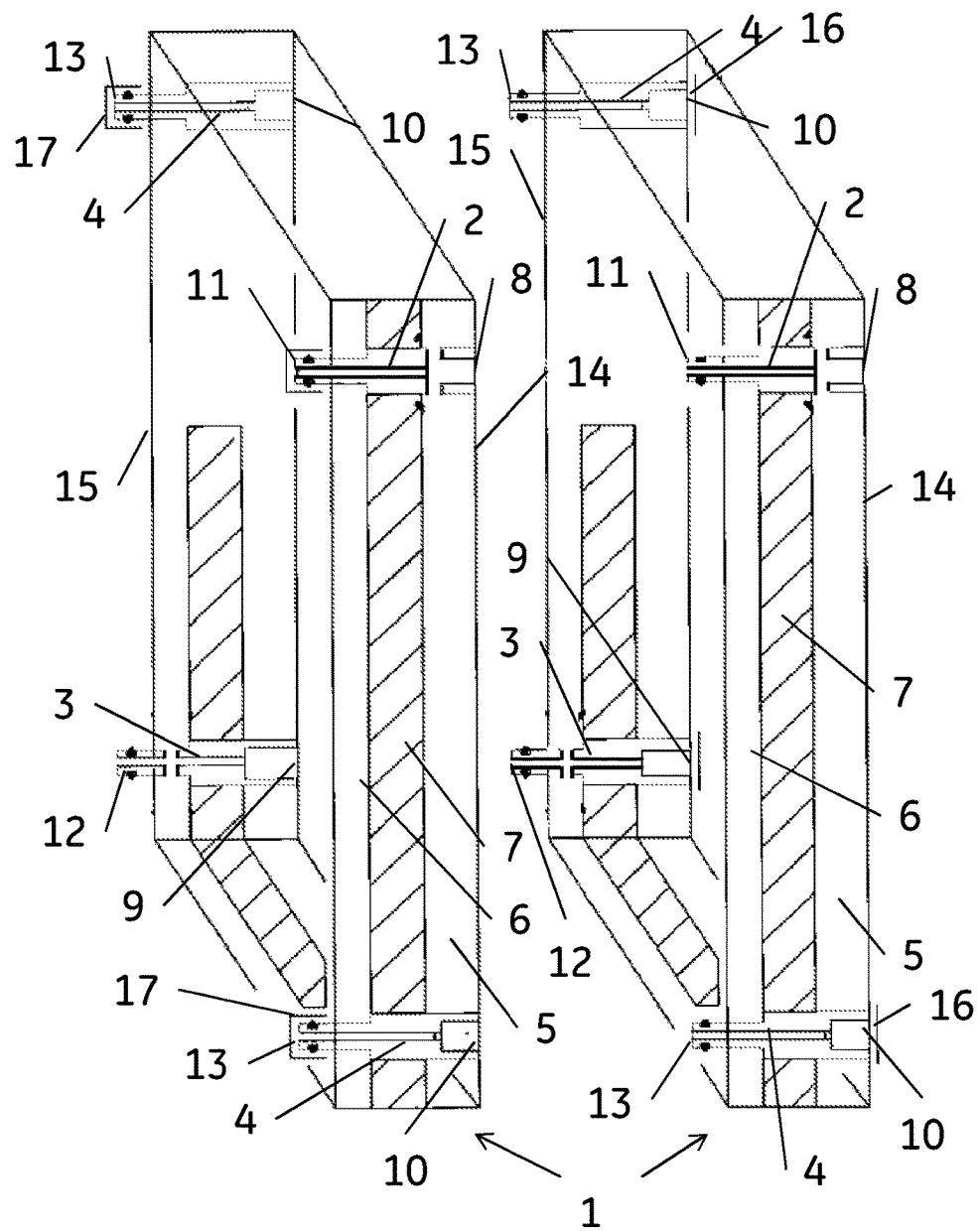
FIG. 2 shows an exploded stack of two cassettes according to the invention
Figure 3:
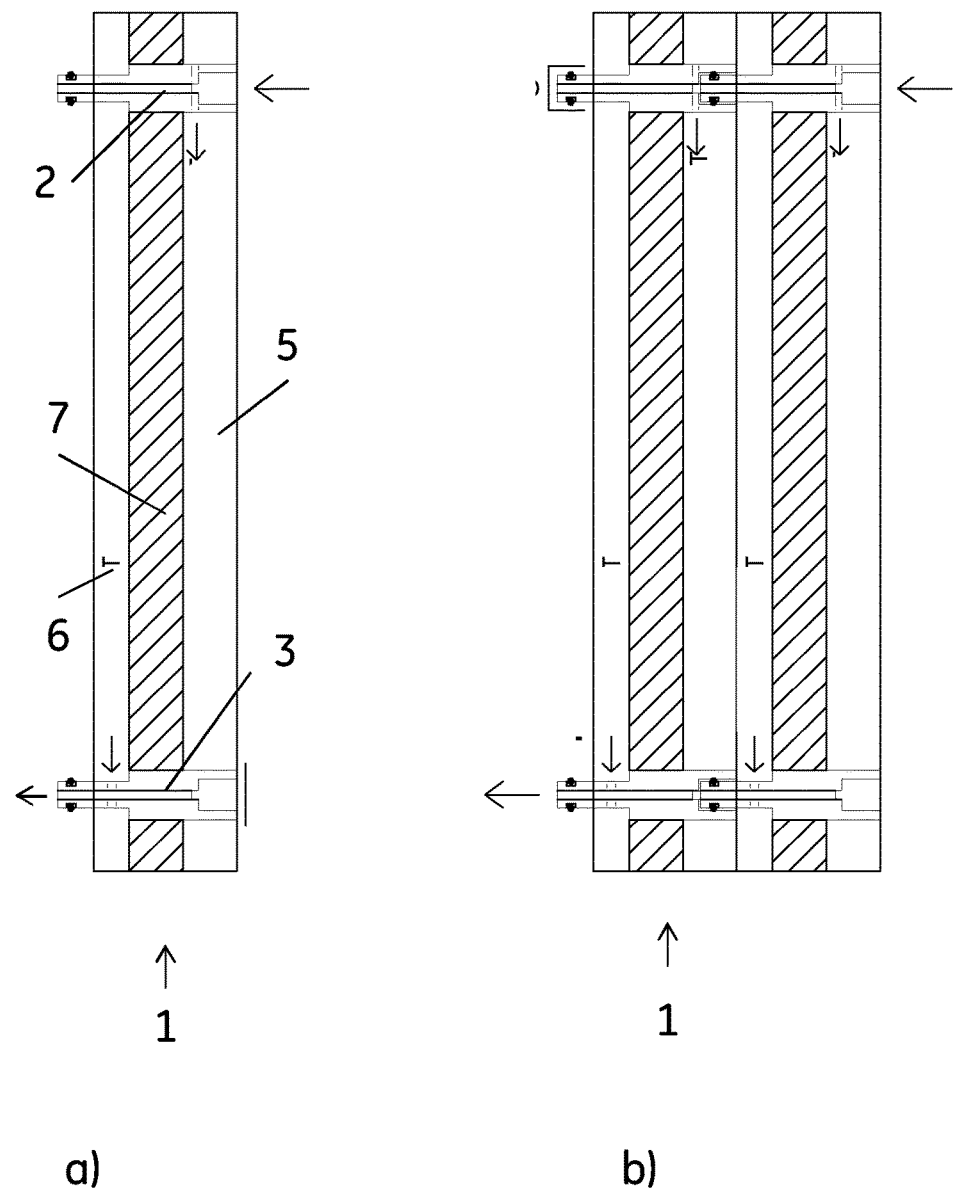
FIG. 3 shows a cassette according to the invention and a stack of two cassettes according to the invention.

The term "normal flow filtration" herein means a filtration process where the entire feed stream applied to a filter device, such as a cassette, flows through the filter medium. This is in contrast to tangential flow filtration (also called crossflow filtration) where a substantial part of the feed stream is recirculated and only part of it flows through the filter medium. Normal flow filtration is typically used in depth filtration and in some membrane microfiltration applications.

The term "depth filter" herein means a thick (at least 0.5 mm) filter that is able to capture contaminant particles within its pore structure by entrapment and/or adsorption.

DETAILED DESCRIPTION OF EMBODIMENTS

In one aspect, illustrated by FIGS. 1-5, the present invention discloses a normal flow filtration cassette (1), which is stackable with like cassettes. The cassette comprises at least three port conduits (2,3,4), an inlet chamber (5) which is in fluid communication with at least a first of the port conduits (2) and an outlet chamber (6) which is in fluid communication with at least a second of the port conduits (3). It also comprises a filter medium (7) between the inlet chamber (5) and the outlet chamber (6). The filter medium can be sealed to a sealing frame (98), which in turn is sealed to the side walls (97) of the cassette such that the flowpath from the inlet chamber to the outlet chamber passes through the filter medium. Alternatively, the filter medium can be directly sealed to the side walls of the cassette. The heights of the inlet and outlet chambers can be at least 1 mm, such as between 2 and 10 mm or between 3 and 8 mm, to provide an unimpeded flow rate. The three port conduits (2,3,4) are each in fluid communication with a corresponding inlet port (8,9,10) and are also each in fluid communication with one of a corresponding set of outlet ports (11,12,13). Each of the set of inlet ports (8,9 10) is arranged to cooperate with a respective complementary outlet port of an adjacent like cassette when in a stack and the outlet ports (11,12,13) are each arranged to cooperate with a respective complementary inlet port of a further adjacent like cassette when in a stack. The cooperation may be in the form of mating cooperation, e.g. with male outlet ports mating with female inlet ports. Each port conduit may be integrally formed with the corresponding inlet and outlet ports as a port post (96). The port post can be a load-bearing structure and can also define the height of the cassette as well as the heights of the inlet and outlet chambers. This provides for simple and cost-effective construction and assembly of the cassette, as well as for mechanical robustness. As an example, illustrated in FIG. 1, the cassette can be assembled from a filter medium (7), a support screen (99), a sealing frame (98), at least three (such as four) port posts (96) and an inlet side cover piece (95) and an outlet side cover piece (94). The support screen, sealing frame, port posts and inlet and outlet cover pieces can all be made from thermoplastic materials, enabling assembly by welding.

In certain embodiments, a third of the at least three port conduits (4) is fluidly isolated from the inlet chamber (5) and the outlet chamber (6). This allows flow to bypass the cassette, such that e.g. parallel access to several sets of serially coupled cassettes can be achieved. The cassette may also comprise a fourth port conduit (4), fluidly isolated from the inlet and outlet chambers, allowing further flexibility in arranging the flowpaths of cassette stacks.

In some embodiments, the inlet ports (8,9,10) are arranged as recesses in an inlet side (14) of the cassette and the outlet ports (11,12,13) are arranged as protrusions on an outlet side (15) of the cassette. The inlet ports can thus be arranged as female ports capable of mating with the outlet ports arranged as male ports. An advantage of this is that the cassettes can be fixed to each other, requiring only light clamping to keep the stack together during use. The inlet and outlet ports can also interlock by e.g. snap action or other locking means, totally avoiding the need for clamping. The outlet and/or inlet ports may also comprise sealing means to prevent fluid leakage from the cooperating or mated ports. The sealing means can be e.g a gasket or O-ring, e.g. an O-ring mounted in a recess on each outlet port, or it can be a portion of elastomeric material integrally formed with a port.

In certain embodiments, at least one of the inlet ports is closed with a plug (16) and/or at least one of the outlet ports is closed with a cap (17). Plugs and caps can be used e.g. on the first and last cassettes in a stack in order to direct the flow to specific flowpaths and to block the outflow from selected flowpaths such that the flow is forced through the filter media in selected cassettes. It is also possible to use specially designed plugs and/or caps on cassettes in the interior of the stack to create specific flowpath patterns.

Figure 4:
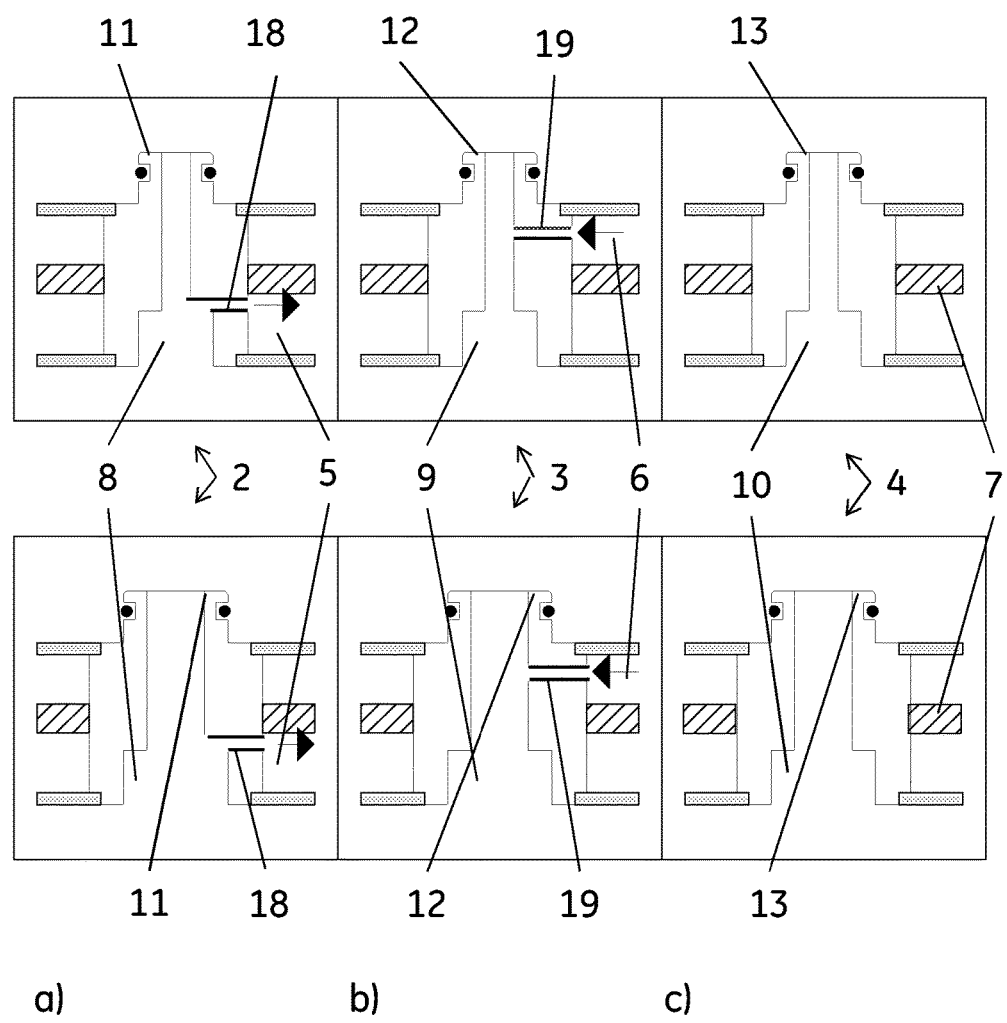
FIG. 4 shows an enlargement of the port conduits of FIGS. 1-3. a) in fluid communication with the inlet chamber, b) in fluid communication with the outlet chamber and c) fluidically isolated from the inlet and outlet chambers. The top set shows port conduits for smaller cassettes, with lower cross-section diameters than the bottom set.

In some embodiments, a slit opening (18) in a wall of at least the first of the port conduits (2) provides fluid communication with the inlet chamber and a slit opening (19) in a wall of at least the second of the port conduits (3) provides fluid communication with the outlet chamber. As illustrated in FIG. 4, the diameters of the port conduits may varied according to the intended flow rates in the cassettes. The slit shaped openings are convenient for manufacturing by e.g. injection molding and provide a good trade-off between mechanical stability and open area.

In certain embodiments, the filter medium is a sheet of filter medium and the cassette further comprises a support screen (99) between the sheet (7) of filter medium and the outlet chamber (5). A support screen provides mechanical support for non self-supporting filter media. The pores of the support screen can suitably be substantially larger than those of the filter medium. Support screens can be selected from e.g. woven or non-woven textile materials, extruded screens, sintered materials etc. which are well known in the art of filtration.

In some embodiments, the filter medium or sheet of filter medium (7) comprises a depth filter pad, such as e.g. a fibrous depth filter pad or a porous polymer pad. The thickness of the depth filter pad may be e.g. 0.5-20 mm, such as 1-15 or 2-15 mm. If the depth filter is a fibrous depth filter pad it may comprise fibers, such as cellulose fibres or glass fibres, and optionally other components such as filter aids, porous particles, charge modification agents etc. If the depth filter pad is a porous polymer pad it may comprise a polymer foam, a porous sintered polymer or a porous polymer prepared by phase separation. It may also in this case further comprise other components such as filter aids, porous particles, charge modification agents etc. Different types of depth filter media useful in the invention are discussed in e.g. M Prashad, K Tarrasch: Filtration+Separation 28-30 Sep. 2006 and T E Arnold: BioProcess Int 44-49 2005. The pore size rating of the depth filter media can e.g. be in the range of 0.1-70 micrometers, such as 0.1-20 or 0.2-10 micrometers, and the pore structure may be either homogeneous or forming a transverse gradient through the medium—typically with smaller pores at the filtrate side. The pore surface charge may be positive, neutral or negative. Charged pore surfaces, in particular positively charged pore surfaces, can enable capture of particles larger than the pores of the filter medium. Specific examples of useful filter media include the Seitz Bio-, K-, P-, T- and Z-series of filter sheets from Pall Corporation, the ZetaPlus™ VR or EXT-series of filter media from 3M. The pore size rating is measured by challenging the filter medium with liquids containing particles of different sizes (typically expressed as volume-weighted particle diameter averages) and determining the smallest particle size that is retained by the filter. The pore surface charge can be measured e.g. by streaming potential measurements.

The cassette may also comprise more than one filter medium, e.g. a coarse medium followed by a finer medium. It can also comprise a microporous membrane, either as a single filter medium or in combination with a depth filter medium.

In certain embodiments the inlet (8,9,10) and outlet (11,12,13) ports are hermetically sealed with removable sanitary film covers. The covers provide protection against external contamination of the cassette interior. This is important in a bioprocess setting where contamination with potential pathogens and other undesirable materials must be avoided. The covers are also particularly useful in order to maintain sterility of a presterilized cassette. To maintain sterility throughout the operation of assembling a stack of cassettes, the sanitary film covers can suitably be arranged as described in U.S. Pat. No. 6,679,529, WO1994008173 or WO1996030076, which are all incorporated by reference in their entirety, such that they can be pulled off at the moment when the inlet and outlet ports are in contact and the ports get in sealing cooperation immediately when the covers are pulled off.

In some embodiments, the cassette is radiation sterilized. Radiation sterilization can be achieved by exposing the cassette ionizing radiation, e.g. gamma or electron beam radiation with a dose sufficient to impart sterility. To maintain sterility of the cassette, the ports of the cassette can before sterilization be hermetically sealed as described above. Alternatively, the cassette can be packed in a hermetically sealed bag. In the latter case, the stack of cassettes may have to be assembled in a sterile space.

In certain embodiments the cassette comprises four port conduits. A fourth port conduit is useful for creating more complex flowpaths, e.g. when a stack of cassettes comprises cassettes with three different filter media. It can also be used in parallel with another port conduit of the same cassette to increase the flowrate. In this way it can e.g. be used to double up the inlet stream, the primary filtrate stream and/or the secondary filtrate stream.

In some embodiments the cassette is generally rectangular or a generally rectangular parallelepiped. The shape or cross section can e.g. be rectangular, quadratic, rectangular/quadratic with cut or curved corners etc. The port conduits can be located adjacent the corners of the cassette, such as with one port conduit adjacent each corner. This allows for a good flow distribution in the cassette and, if the port conduits with the ports are constructed as load-bearing port posts, it also allows for good mechanical properties of the cassette.

In the embodiments described above, the cassette may further comprise one or more sensors, e.g. pressure sensors in the inlet and outlet chambers for monitoring of the back pressure over the filter medium and any tendency for clogging. Other sensors, e.g. turbidity sensors, can also be used to monitor the filtration effect during use of the cassette. Alternatively, or additionally, the cassette may also comprise one or more sampling ports for taking samples during filtration, e.g. in order to assess the effect of filtration on a feed.

In a second aspect, illustrated by FIGS. 5-8, the present invention discloses a stack (20;40) comprising at least two, such as at least three or four, or 2-24, cassettes (21,22;41-44) according to any embodiment disclosed above, wherein the inlet (27-30;47-50) and outlet (31-34;51-54) ports on adjacent cassette surfaces (25,26; 45,46) are in mating cooperation with each other.

Figure 6:
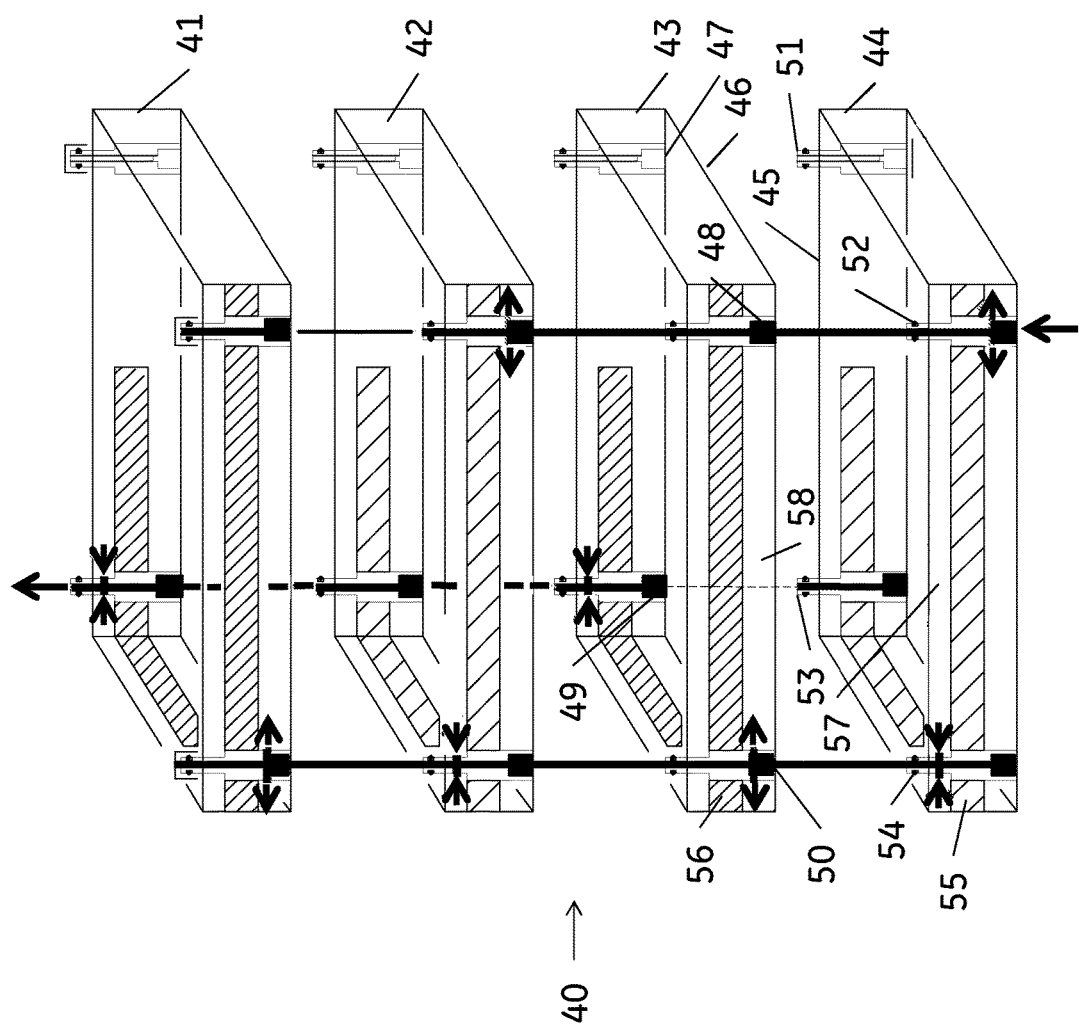
FIG. 6 shows an exploded view of a four-cassette stack according to the invention, with two different filter media in the cassettes.
Figure 7:
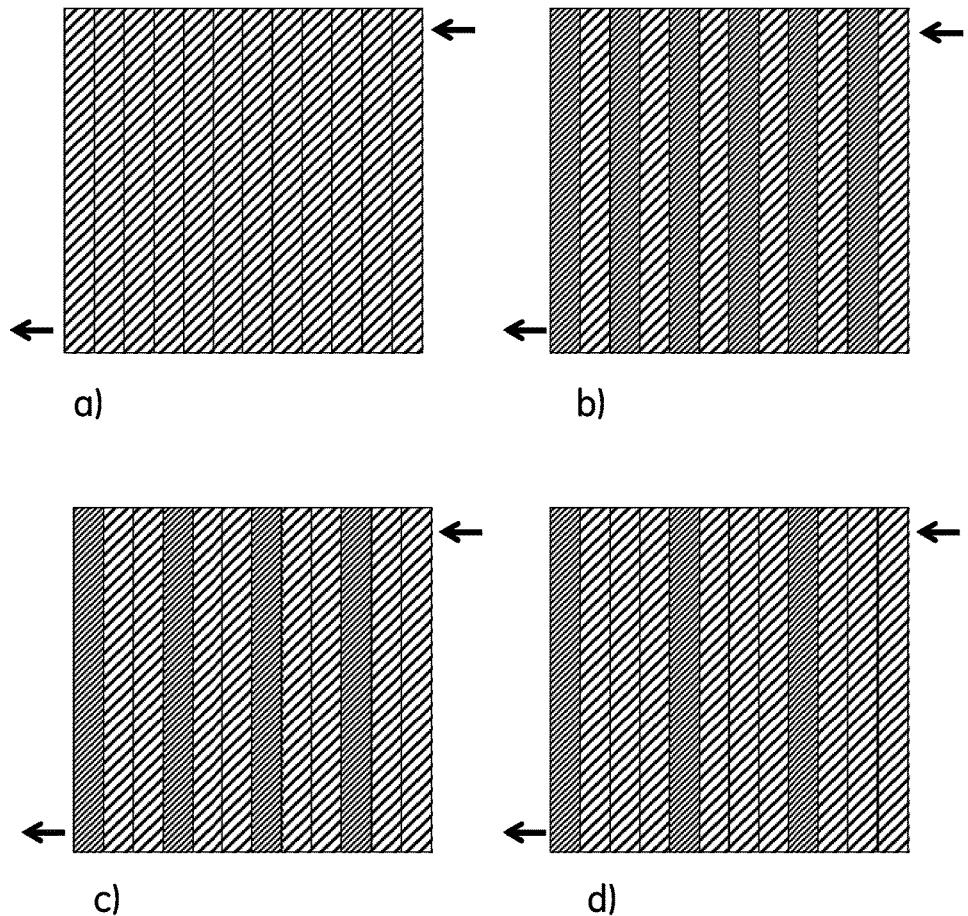
FIG. 7 shows four twelve-cassette stacks according to the invention: a) one filter medium, b) six parallel substacks, each containing one coarse and one fine cassette, c) four parallel substacks, each containing two coarse and one fine cassette and d) three parallel substacks, each containing three coarse and one fine cassette.
Figure 8:
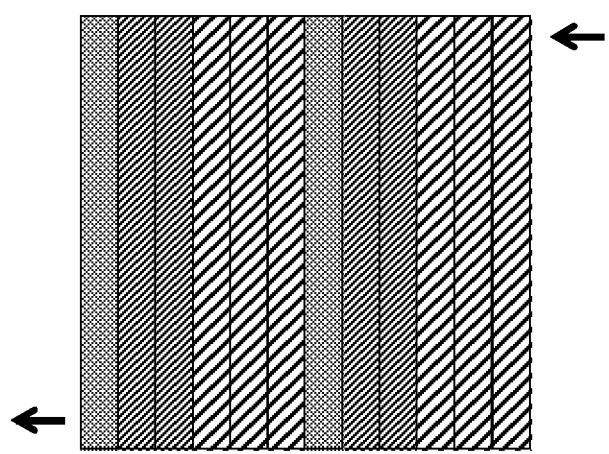
FIG. 8 shows a twelve-cassette stack according to the invention with two parallel substacks, each containing three coarse, two fine and one superfine cassette.

In some embodiments, illustrated by FIGS. 6-8, at least a first cassette (44) comprises a sheet of a first filter medium (55) and at least a second cassette (43) comprises a sheet of a second filter medium (56) which has properties substantially different from the first filter medium. The substantially different properties may include the (nominal) pore size rating, the density, the surface charge and any transverse gradients in pore size, density and/or surface charge. By substantially different can be meant that a property differs by at least 10%, such as by at least 25%. The first and second cassette can be serially coupled, forming a serial train, such that the outlet chamber (57) of the first cassette is in fluid communication with the inlet chamber (58) of the second cassette. The serial train may also comprise a plurality of first cassettes, with the first filter medium, coupled in parallel and all serially coupled with the second cassette having the second filter medium. The stack may comprise a plurality of such serial trains, coupled in parallel. An advantage of these arrangements is that the areas of the first and second filter media can be independently varied, in order to utilize the capacity of the media in the most efficient way.

In certain embodiments the stack further comprises at least a third cassette, which comprises a sheet of a third filter material having properties substantially different from the first and second filter materials as described above. The first, second and third cassette may be serially coupled, forming a serial train—optionally with a plurality of first, second and/or third cassettes coupled in parallel within the train, and several such serial trains may be coupled in parallel within a stack.

Figure 5:
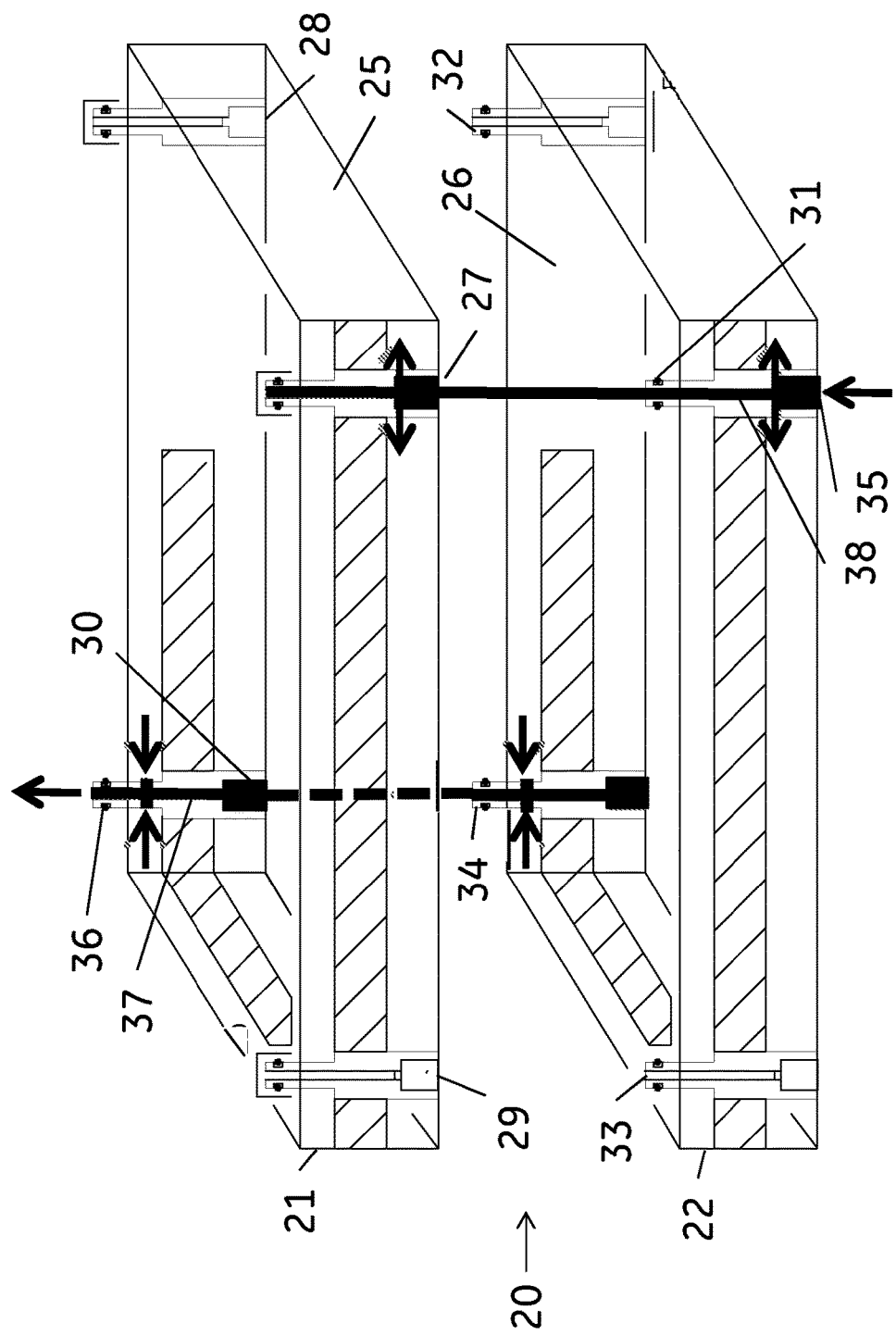
FIG. 5 shows an exploded view of a two-cassette stack according to the invention.

In some embodiments, illustrated by FIG. 5, in one cassette (22) only one inlet port (35) and two outlet ports (31,34), one of which (31) is comprised in the same port conduit (38) as the inlet port (35) are open and in fluid communication with the inlet or outlet chamber; and in an adjacent cassette (21) the only open ports in fluid communication with the inlet or outlet chamber are one inlet port (27) mated with open outlet port (31) of the first cassette, the inlet port (30) mated with open outlet port (34) of the cassette (22) and one outlet port (36) comprised in the same port conduit (37) as open inlet port (30).

In certain embodiments, illustrated by FIGS. 6-8, the outlet chamber (57) of a one or more first cassette (44) comprising a sheet of a first filter medium (55) having a first pore size rating is in fluid communication with the inlet chamber (58) of a second cassette (43) comprising a sheet of a second filter medium (56) having a second pore size rating which is at least 10%, such as at least 25%, smaller than the first pore size rating, e.g. with the first filter medium having a pore size rating of about 10 micrometers and the second filter medium having a pore size rating of about 0.5 micrometers. The stack may comprise a plurality of such serial trains, coupled in parallel.

In some embodiments the fluid communication between the outlet chamber of the first cassette and the inlet chamber of the second cassette is provided via a port conduit of another cassette, which port conduit is fluidly isolated from the inlet and outlet chambers of this cassette.

FIG. 7 illustrates stacks comprising cassettes with coarse and fine filter media. In FIG. 7 a, the stack contains 12 cassettes with coarse filter medium, coupled in parallel. The stack of FIG. 7 b contains six serial trains, coupled in parallel, where each train contains one cassette with coarse medium followed by one cassette with fine filter medium. In FIG. 7 c, the stack contains four serial trains, coupled in parallel, with two parallel coarse cassettes followed by one fine cassette in each train. The stack of FIG. 7 d has three serial trains in parallel, with each train containing three parallel coarse cassettes followed by one fine cassette. FIG. 8 illustrates a stack with two serial trains coupled in parallel, where each train starts with three parallel coarse cassettes, followed by two parallel fine cassettes and finally by one superfine cassette.

The stack can be arranged by plugging and capping to have one open inlet and one open outlet. The open inlet and the open outlet may be equipped with sanitary connectors which are hermetically sealed with removable sanitary film covers. Such connectors are described in U.S. Pat. No. 6,679,529 and WO1994008173A1, which are hereby incorporated by reference in their entirety. They are commercially available e.g. as ReadyMate™ (GE Healthcare) and can be connected to the ports e.g. via tubing. An assembled stack with sanitary connectors can be sterilized, e.g. by radiation or steam sterilization and connected to a circuit under sterile conditions by removing the film covers during connection.

In a third aspect the present invention discloses a method for clarification of a bioprocess feed which comprises the steps of:
a) providing a cell culture broth,
b) optionally pretreating said cell culture broth by centrifugation or cell settling,
c) passing said broth through a stack according to any one of the embodiments disclosed above.

The cell culture broth may contain a biopharmaceutical such as an expressed protein—e.g. an antibody, an antibody fragment, a fusion protein—or a vaccine antigen—e.g. virus particles, polysaccharides, a plasmid etc. The cells used may be animal cells, e.g. mammalian cells such as CHO cells or insect cells or they may be microbial cells, e.g. bacterial or yeast cells. A pretreatment step involving centrifugation or gravity settling may be used to lower the amount of cells and cell debris before filtration. The stack of cassettes may be arranged with different filter media in such a way that the capacity of the media, e.g. coarse and fine media is utilized in an optimal way. It may e.g. be arranged such that the area ratio between the coarse and fine filter media is larger than 1:1, such as 2:1, 3:1 or 4:1.

In a fourth aspect the present invention discloses a method for selecting a stack for the clarification of a bioprocess feed comprising the steps of:
a) providing a cell culture broth,
b) optionally pretreating said cell culture broth by centrifugation or cell settling,
c) assembling a plurality of stacks with different sequences of cassettes, comprising first, second and optionally third filter media or sheets of filter medium, with substantially different properties, as described above,
d) passing an aliquot of said cell culture broth through each of said stacks and measuring the flow rate decay or back pressure build-up and,
e) using the flow rate decay or back pressure build-up data to select a stack with a particular sequence.

The stacks may be assembled so as to obtain a diversity in the area ratios between the different filter media. This allows an efficient optimization of the filtration process for a given feed, using either flow rate decay (from a constant pressure filtration experiment) or back-pressure build-up (from a constant flow rate filtration experiment) as an output variable to detect clogging of the filters. It is also possible to use clarity of the filtrates obtained from the stacks or from samples taken after individual cassettes, e.g. measured by turbidimetry, as an output variable in the optimization.

If one or more of the cassettes in the stack comprises sensors as described above, it is possible to monitor the individual performance of cassettes in the stack with time, e.g. to see in which cassettes clogging occurs first (as monitored by an early increase in back pressure or an early loss of flow rate). Measuring back pressure build-up or flow rate decay over one or more individual cassettes in step c) will provide very useful data for step d), but it is not a necessity. It is also possible to measure back pressure build-up/flow rate decay over the entire stack in step c) and to use these data in step d).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Features from different embodiments and aspects of the invention may be combined with each other to create further embodiments.

All publications, patent publications, and patents are herein incorporated by reference to the same extent as if each individual publication or patent was specifically and individually indicated to be incorporated by reference.

What is claimed is:

1. A normal flow filtration cassette stackable with an adjacent normal flow filtration cassette to form a filtration cassette stack, said normal flow filtration cassette comprising: one or more inlet ports; one or more outlet ports; at least three port conduits; an inlet chamber in fluid communication at least with a first port conduit of said at least three port conduits; an outlet chamber in fluid communication at least with a second port conduit of the at least three port conduits; and a filter medium between said inlet chamber and said outlet chamber, wherein each port conduit of said at least three port conduits is in fluid communication with a corresponding inlet port of said one or more inlet ports and is in fluid communication also with a corresponding outlet port of said one or more outlet ports, and wherein each inlet port of said one or more inlet ports is arranged to cooperate with a respective complementary outlet port of the adjacent normal flow filtration cassette when in the formed filtration cassette stack and said each outlet port of said one or more outlet ports is arranged to cooperate with a respective complementary inlet port of a further adjacent normal flow filtration cassette when in the formed stack, wherein a third port conduit of the at least three port conduits is fluidly isolated from the inlet chamber and the outlet chamber.

2. The cassette according to claim 1, wherein said each inlet port of the one ore more inlet ports is arranged as a recess in an inlet side of said cassette and said each outlet of the one or more outlet ports is arranged as a protrusion on an outlet side of said cassette.

3. The cassette according to claim 2, wherein one of the one or more inlet ports is closed with a plug and/or one of the one or more outlet ports is closed with a cap.

4. The cassette according to claim 1, wherein a slit opening in a wall of the first port conduit of the at least three port conduits provides fluid communication with the inlet chamber and a slit opening in a wall of the second port conduit of the at least three port conduits provides fluid communication with the outlet chamber.

5. The cassette according to claim 1, wherein said filter medium is a sheet of filter medium and the cassette further comprises a support screen between said sheet and said outlet chamber.

6. The cassette according to claim 1, wherein said filter medium comprises a depth filter pad.

7. The cassette according to claim 1, wherein said one or more inlet ports and one or more outlet ports are hermetically sealed with removable sanitary film coven.

8. The cassette according to claim 1, wherein the cassette is radiation sterilized.

9. The cassette according to claim 1, wherein the cassette comprises four port conduits.

10. The cassette according to claim 1, wherein the cassette rectangular.

11. The cassette according to claim 10, wherein each port conduit of the at least three port conduits is located adjacent corners of said normal flow filtration cassette.

12. A stack comprising at least two normal flow filtration cassettes according to claim 1, said at least two cassette comprises a first cassette and an adjacent second cassette, wherein the inlet and outlet ports of the first cassette and corresponding outlet and inlet ports of the adjacent second cassette are in mating cooperation with each other.

13. The stack according to claim 12, wherein the first cassette comprises a first filter medium or a sheet of filter medium having a first pore size rating and the second cassette comprises a second filter medium or a sheet of filter medium with properties different from the first filter medium or sheet of filter medium.

14. The stack according to claim 13, further comprising a third cassette, which comprises a third filter medium or sheet of filter medium with properties different from said first and second filter media or sheets of filter medium.

15. The stack according to claim 12, wherein the first cassette comprises a first inlet port and two outlet ports, wherein a first outlet port of said outlet ports is comprised in the same port conduit as the first inlet port so as to be in open and in fluid communication with the inlet or outlet chamber of said first cassette; and wherein the adjacent second cassette comprises a second inlet port mated with first outlet port of the first cassette, the second inlet port mated with open outlet port of the first cassette and a second outlet port of the second cassette comprised in the same port conduit as the second inlet port.

16. The stack according to claim 12, wherein the outlet chamber of the first cassette comprising a first filter medium or sheet of filter medium having a first pore size rating is in fluid-communication with the inlet chamber of the second cassette comprising a second filter medium or sheet of filter medium having a second pore size rating which is at least 10% smaller than the first pore size rating.

17. The stack according to claim 16, wherein the fluid communication between the outlet chamber of the first cassette and the inlet chamber of the second cassette is provided via a port conduit of another cassette, which port conduit is fluidly isolated from the inlet and outlet chambers of this cassette.

18. The cassette according to claim 6, wherein the depth filter pad comprises a fibrous depth filter pad or a porous polymer depth filter pad.

* * * * *